United States Patent [19]
Dixon

[11] Patent Number: 5,133,706
[45] Date of Patent: Jul. 28, 1992

[54] DISPOSABLE DIAPER WITH TAB FASTENER

[76] Inventor: Robert Dixon, Yarmouth, Mass.

[21] Appl. No.: 347,726

[22] Filed: May 5, 1989

[51] Int. Cl.⁵ .............................. A61F 13/15;
[52] U.S. Cl. ................................ 604/389
[58] Field of Search ............ 604/389, 390, 391; 128/158

[56] References Cited

U.S. PATENT DOCUMENTS

| | | | |
|---|---|---|---|
| 3,646,937 | 3/1972 | Gellert | 604/390 |
| 3,948,258 | 4/1976 | Karami | 604/390 |
| 4,413,621 | 11/1983 | McCraeken et al. | 604/390 |
| 4,540,415 | 9/1985 | Korpman | 604/390 |
| 4,832,008 | 5/1989 | Gilmam | 128/156 |

*Primary Examiner*—David J. Isabella
*Attorney, Agent, or Firm*—Wolf, Greenfield & Sacks

[57] ABSTRACT

A disposable diaper has a tab construction having one end secured thereto and the other free end having a coated segment and a finger gripping segment with the finger segment defined from the coated segment by perforations which permit the removal of the finger gripping section from the tab after the adhesive section is adhered to the diaper.

4 Claims, 1 Drawing Sheet

DISPOSABLE DIAPER WITH TAB FASTENER

SUBJECT MATTER OF INVENTION

The present invention relates to disposable diaper having an improved tab fastener.

BACKGROUND OF THE INVENTION

Disposable diapers have been made with means for securing the diaper in place. Originally, disposable diapers were ordinarily secured by safety pins. More recently, tabs attached to the diaper have replaced safety pins. Tabs in the form of short segments of tape facilitate the application of the diaper and are safer and are less likely to injure an infant wearing the diaper. In developing tabs for use with diapers, there has been a significant effort to make the tab with sufficient structural integrity to resist tearing and thereby preclude the diaper coming loose while on an infant. Such tabs must have a strong bond to the diaper surface which is typically made of plastic. Such efforts, have in general, been successful. Exemplifications of such disposable diapers having tabs are exemplified by U.S. Letters Pat. Nos. 3,869,761, 4,643,729, 3,931,666, 3,989,047, 4,122,552, 4,516,976, 4,540,415, and 4,389,212. Generally, these patents disclose the use of a pair of tabs to secure corner sections of a plastic disposable diaper together. Typically a pair of tabs are attached to a diaper at opposite corners along an upper edge. Each of the tabs are secured at one end to the diaper by an adhesive layer that coats one surface of the tab at one end with the other end projecting outwardly. The adhesive covering the projecting end of the tab is covered with a strippable release sheet having a projecting tip that permits ready removal of the release sheet. In some instances, this release sheet or strip is itself secured to the diaper to form a reinforcement as illustrated in U.S. Pat. No. 4,540,415. In addition, the adhesively coated tabs in many diaper constructions have an end section of the free end uncoated to form a finger grip to assist in stripping the projecting end from the release sheet. However, when the diaper is applied to an infant and the free end of the tab is secured to an opposite portion of the diaper, the uncoated end section of the tab at the free end, forming the finger grip, does not adhere to the diaper. Unfortunately, this projecting finger grip is frequently rubbed or grabbed by the infant while wearing the diaper. As a result, diapers having finger grips are frequently removed by the infant with obvious undesirable results. Similar problems exist with respect to diapers worn by the senile or mentally impaired. It is estimated as many as 35% of these people remove their diapers with similar results.

Attempts to avoid these problem have taken several forms. In some diapers there is no finger grip formed. Such diapers are inconvenient to apply because there is nothing to hold but the sticky end of the tab when applying it. Additionally, the projecting end is difficult to free from the release sheet when applying the diaper. In another diaper construction a weakened section is formed in the tab. This weakened section is covered by another adhesive tab. This arrangement is illustrated in U.S. Letters Pat. No. 3,869,761. Unfortunately, this diaper has defects similar to those of diapers with non-adhesive sections at the end of the tab, because the re-enforcing section itself has a finger tab which can be easily grasped or removed by an infant, thus leaving exposed a weakened section of the closing tab.

It is an object of the present invention to provide an improved disposable diaper construction having integrally formed attaching tabs on the diaper.

A further object of the present invention is to provide an improved tab construction for disposable diapers which are difficult to inadvertently strip and thereby open the diaper.

A further object of the present invention is to provide an improved tab construction for disposable diapers in which means are provided for easy removal of the release sheet while still providing means by which the tabs can be secured to the diaper without inadvertent opening of the tabs by the infant.

A further object of the present invention is to provide an improved tab construction for a diaper in which the entire length of the tab is secured by an adhesive surface to the diaper when the diaper is properly positioned on an infant, while still providing an improved means for removing the release paper from the adhesive surface of the tab prior to application.

BRIEF SUMMARY OF THE INVENTION

The present invention overcomes the problems referred to above by providing a tab construction for disposable diapers in which the free end of the adhesive tab is formed as a finger grip constructed in such a fashion that an infant cannot accidentally engage it to remove or loosen the tab when the diaper is being worn.

In the present invention there is provided, in the preferred embodiment of the invention, a tab construction having one end secured to a diaper and the other free end having a coated segment and a finger gripping segment with the finger gripping segment defined from the coated segment by perforations which permit the removal of the finger gripping section from the tab after the adhesive section is adhered to the diaper.

DESCRIPTION OF THE DRAWINGS

The foregoing objects and advantages of the present invention will be more clearly understood when considered in conjunction with the accompanying drawings in which.

DETAILED DESCRIPTION OF THE INVENTION

Figure 1:
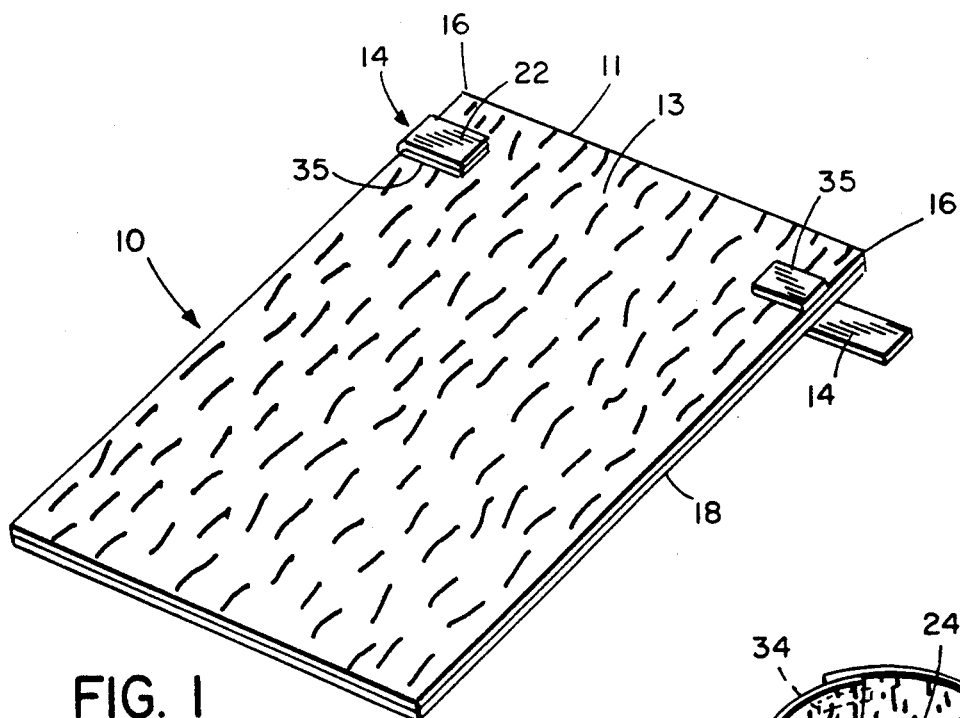
FIG. 1 is a perspective view of a diaper, in accordance with a preferred embodiment of the present invention.

As illustrated in FIG. 1, a disposable diaper 10 is provided with a pair of pressure sensitive tabs 14, preferably at one end of the diaper 10. One of the tabs 14 in one section of the diaper is preferably aligned with the other of the tabs along a common edge 11 of the diaper. Each tab 14 is secured to the backing sheet 18, which in most disposable diapers is made of a moisture impermeable polyetheylene material. Diaper 10 is typically also made with a facing sheet 13 that is moisture permeable, and with an absorbent batt sandwiched between the facing sheet 13 and the moisture impermeable sheet 18.

Tabs 14 extend outwardly from opposite edges near corner sections 16 adjacent end edge 11 of the diaper.

The tabs 14 are each preferably formed of a relatively strong flexible plastic sheet adapted to be coated with adhesive suitable to secure it to the diaper. These tabs are preferably rectangular in shape with at least a portion of one end 22 on one side of the center indicated by a dotted line 23, secured by an appropriate adhesive layer 27 on one surface to the backing 18 of the diaper. A securing portion 24 on the other side of the center line 23 is also covered with the adhesive layer 27. The adhesive layer 27 however does not cover the length of the tab but only extends to a perforation 34 that defines a finger gripping portion 26 that is devoid of pressure sensitive adhesive. The portion 26 is located at the end edge of the tape remote from the one end 22. A release sheet 35 is secured to the facing sheet 13 in alignment with the one end 22 which is secured on the opposite side to backing sheet 18. The one end 22 is folded over and strippably adhered to the release sheet 35 except for the finger gripping portion 26.

Adhesive tabs suitable for the purpose of the present invention may be made from a wide variety of material provided the material is sufficiently flexible and strong enough to withstand the normal stresses when the tab is used for securing purposes. For example, the tab 14 including the end 22, securing portion 24, and finger grip portion 26, may be made of cloth, saturated paper, film, foil, plastic or the like. In any event, the tab must be capable of being coated with and secured by a pressure sensitive adhesive. Any adhesive composition that affixes the one end 22 of the tab 14 to the moisture impervious backing 18 is suitable. The adhesive should preferably permit stripping the securing portion 24 from backing 18 to reopen the diaper. As noted above, the finger gripping portion 26 should be free of adhesive. The finger gripping portion 26 which is defined from the securing portion 24 by line of perforation 34 may be severed from the tab by finger pressure or tearing. In place of a perforation a weakened line may be used.

Figure 3:
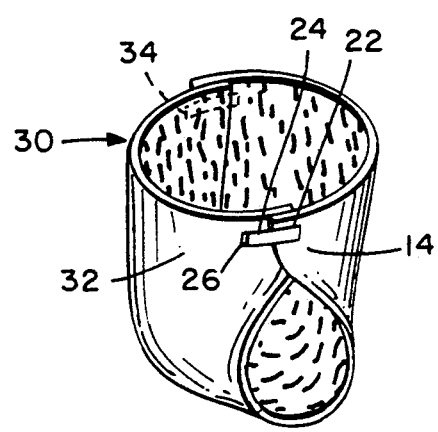
FIG. 3 is a perspective view of a diaper of the present invention in a shape assumed by the diaper when applied to an infant.
Figure 2:
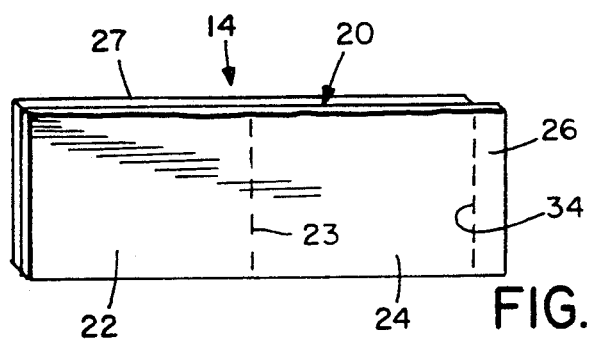
FIG. 2 is an enlarged plan view of the tab used in the preferred embodiment of the present invention.
Figure 4:
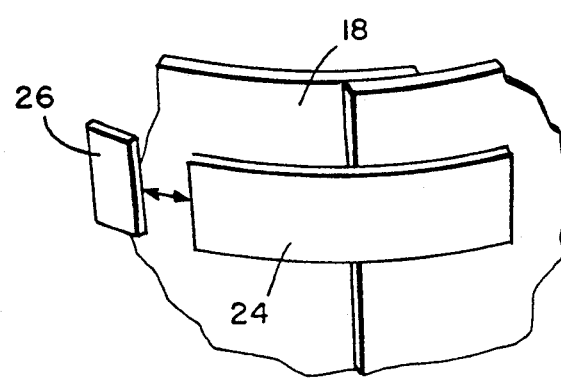
FIG. 4 is perspective fragmentary enlarged view of the tab arrangement illustrated in FIG. 3, with the free end removed.

In use, the diaper is fitted about the infant. The release sheet 35 is removed by grasping the finger gripping portion 26. At that point, the adhesive surface 27 over portion 24 is pressed against an opposite section of the diaper so that the tabs 14 assume the position illustrated in FIG. 3. In this position the finger gripping portion 26 which has been used to assist in stripping from the release coating 35 and in positioning the tab on the diaper may be removed by tearing the finger gripping portion 26 along the line of perforation 34. In that position the entire adhesive surface 27 of the securing portion 24 is adhered to the backing 18 of the diaper so that there are no free edges of corners that the infant may inadvertently grasp. The finger tab 26 is entirely removed and discarded. Thus there is no means by which the infant may inadvertently grasp a loose end of the tab and remove it while the diaper is being worn.

When it is time to remove the diaper, the parent may simply remove it by working loose the tab at its center portion 23.

Having thus described my invention I claim:

1. In a disposable diaper having a pressure sensitive tab for closing said diaper, said tab having one end secured to one section of said diaper and a free end extending from said one section, said free end having a securing portion coated with a pressure sensitive adhesive adapted to adhere to a second section of said diaper and a finger gripping portion adjacent securing portion devoid of pressure sensitive adhesive, a release sheet strippably covering said pressure sensitive adhesive, and means integral with said tab for severing said finger gripping portion from said securing portion after said securing portion has been adhered to said second section of said diaper.

2. A construction as set forth in claim 1 wherein said means for severing said finger gripping portion comprises a line of weakened line through said tab and defining said securing portion from said finger gripping portion.

3. A construction as set forth in claim 2 having a pair of pressure sensitive tabs secured to said diaper at opposite ends of a common edge.

4. A construction as set forth in claim 2 wherein said pressure sensitive tab has an elongated rectangular shape with said weakened line comprising perforations extending across the width of said tab closer to the free end of the tab than the opposite end of the tab.

* * * * *